United States Patent [19]

Hilmersson et al.

[11] Patent Number: 4,512,935
[45] Date of Patent: Apr. 23, 1985

[54] APPARATUS FOR THE VOLATILIZATION OF A LIQUID

[75] Inventors: Anders Hilmersson, Helsingborg; Jan Lagerstedt, Malmö; Helge Andersson, Lund, all of Sweden

[73] Assignee: Tetra Pak International AB, Lund, Sweden

[21] Appl. No.: 570,491

[22] Filed: Jan. 13, 1984

[30] Foreign Application Priority Data

Jan. 25, 1983 [SE] Sweden ................................ 8300356

[51] Int. Cl.³ .............................................. A61L 2/22
[52] U.S. Cl. ................................. 261/79 A; 261/115; 422/306
[58] Field of Search ................ 261/79 A, 115; 422/4, 422/28, 306

[56] References Cited

U.S. PATENT DOCUMENTS

| | | | |
|---|---|---|---|
| 1,253,766 | 1/1918 | Alden | 261/79 A |
| 2,817,415 | 12/1957 | Sykes | 261/79 A |
| 2,935,840 | 5/1960 | Schoppe | 261/79 A |
| 3,481,689 | 12/1969 | Rosdahl et al. | 422/28 |
| 3,771,260 | 11/1973 | Arenson | 261/79 A |
| 3,911,642 | 10/1975 | Ernstsson et al. | 422/22 |
| 4,169,123 | 9/1979 | Moore et al. | 422/28 |
| 4,203,961 | 5/1980 | Cowley | 261/79 A |
| 4,424,189 | 1/1984 | Hick | 422/28 |

Primary Examiner—Ivars Cintins
Attorney, Agent, or Firm—Burns, Doane, Swecker & Mathis

[57] ABSTRACT

The presterilization of packaging machines for the manufacture of aseptic packing containers can be carried out with the help of sterile air and liquid sterilizing agent, which are blended so that a gas saturated with sterilizing agent of a suitable temperature and dew point is obtained. In order to achieve a rapid and effective volatilization of the liquid a circulating movement is imparted to the hot sterile air as the sterile liquid is introduced into the center of the circulating movement. An apparatus using this method comprises a chamber with a helical guide rail and a spray nozzle for the sterilizing liquid.

3 Claims, 1 Drawing Figure

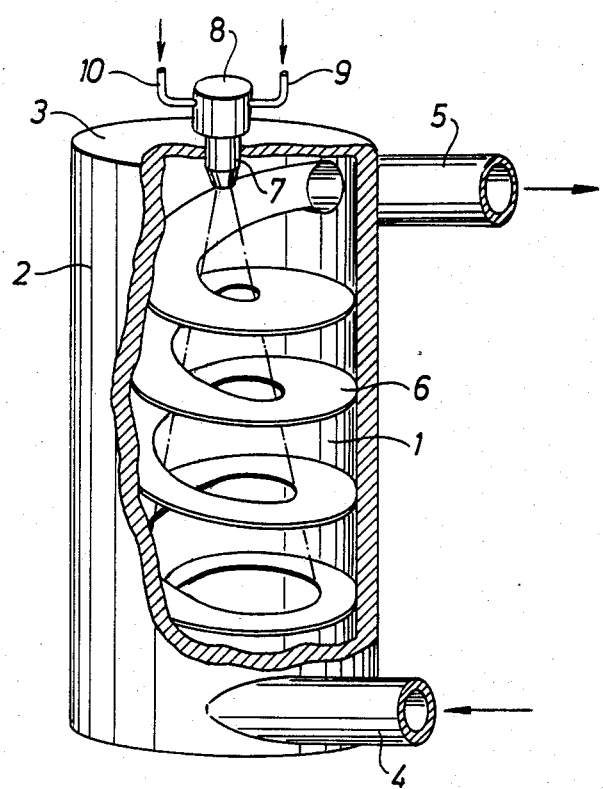

APPARATUS FOR THE VOLATILIZATION OF A LIQUID

BACKGROUND AND SUMMARY OF THE INVENTION

The present invention relates to an apparatus for volatilizing a liquid through blending it with heated gas.

The manufacture of packing containers for products with long keeping quality, such as sterilized juices or the like takes place in packaging machines of the aseptic type. In the packaging machine a material web or material blanks are converted to packing containers which are filled with sterile contents and sealed. The manufacture has to take place under aseptic conditions and the packaging machine thus must be sterilized internally before production commences. This is done preferably by blending a liquid sterilizing agent with hot sterile air so that a gas saturated with sterilizing agent of a suitable temperature and dew point is obtained. As the gas is conducted around the inside of the packaging machine, the sterilizing agent condenses on the relatively cool parts of the machine that come into contact with the gas. As a result a thin, uniform layer of sterilizng agent is formed which sterilizes the surfaces with which the contents or the packing material later will come into contact. Before beginning operation of the packaging machine, the sterilizing agent is removed by hot air which is conducted around the machine so that the sterilizing agent is evaporated again and can be discharged together with the air. In this manner the inside of the machine is sterilized and the production of aseptic packages can commence.

The sterilization method described has been found to work well in practice when the dew point of the gas mixture lies sufficiently high in relation to the temperature of the machine parts to be sterilized. However, if the machine parts to be sterilized are at too high a temperature at the start of the presterilization, condensation will not take place on the surfaces of the parts and the sterilization consequently will be incomplete. This will happen, for example, in machines which are located in abnormally warm localities and in regions with a warm climate. The mixture of sterilizing agent and air which has been used up to now was produced through injection of liquid sterilizing agent into a pipe through which passed a flow of hot sterile air. The maximum dew point of the mixture obtained in this manner is 30-40° C. which in certain cases proves to be insufficient. It has not been possible up to now to obtain by means of the prior art a higher dew point with the large flows which are necessary for the production of sufficient gas quantities.

It is an object of the present invention to provide a method for volatilizing a liquid through blending with heated gas, this method not being subject to the disadvantages of earlier methods.

It is a further object of the present invention to provide a method which makes it possible to volatilize a liquid in a gas and thus produce a mixture of a higher dew point and greater volume per unit of time than had been possible by means of known methods.

It is a further object of the present invention to provide a method for volatilizing a liquid sterilizing agent in hot air, this method being suitable for application in the presterilization of packaging machines of the aseptic type.

These and other objects have been achieved by a method for volatilizing a liquid through blending it with heated gas that is introduced into a chamber where a circulating movement is imparted to it at the same time as the liquid is introduced in the form of drops into the center of the circulating movement.

The method in accordance with the invention makes possible a rapid and complete blending and volatilization of the liquid in the hot gas. As a result, a mixture of a dew point of over 60° C. can be produced very rapidly (over 100 $m^3$ per hour).

It is a further object of the present invention to provide an apparatus for the use of the method that is not subject to the disadvantages of earlier arrangements.

It is a further object of the present invention to provide an apparatus for the volatilization of a liquid in a gas, this apparatus being of simple design and small dimensions which are well suited for application in modern packaging machines.

These and other objects have been achieved with an apparatus comprising a chamber with feed and discharge lines for the gas and a nozzle for the liquid. The chamber is provided with an internal, helical guide rail, the outlet opening of the nozzle being along the geometric center axis of the helical shape of the guide rail.

The apparatus, because of the helical guide rail and the special orientation of the nozzle relatively to the conical center opening of the guide rails, has proved to function very well and to have a high production capacity. The arrangement is without movable parts and is very simple in its design which entails low manufacturing and operating costs.

BRIEF DESCRIPTION OF THE DRAWING

The drawing FIGURE is a schematic representation of the apparatus enclosed in a partially cut away housing.

DETAILED DESCRIPTION OF THE PREFERRED EMBODIMENT

The apparatus comprises a cylindrical blending chamber 1 which is surrounded by a casing with a cylindrical shell wall 2 and end walls 3. The arrangement further comprises feed and discharge lines 4,5, respectively, which are in the form of pipes joining the cylindrical shell 2 tangentially. The feed line 4 is located near the lower end wall of the blending chamber and the discharge line 5 is located near the upper end wall 3 of the blending chamber 1. The cylindrical shell wall 2 as well as the end walls 3 and the lines 4,5 are made of stainless steel, the shell wall 2, for reasons which will be explained in more detail in the following, having a relatively great thickness of approx. 5 mm. The total height of the container is approx. 0.5 m and the diameter of the chamber is 150 mm.

Inside the chamber 1 there is a helical guide rail 6 which runs along the shell surface between the two end walls of the blending chamber. The guide rail 6 is formed from a strip-like plate segment coiled in the form of a helix whose width diminishes successively from approx. 60 mm at the upper end of the blending chamber to approx. 20 mm at the lower end of the blending chamber. Since the guide rail 6 rests with one edge against the inner surface of the shell wall 2, the successively diminishing width means that the guide rail has a centrally located, conical opening whose cone angle is approx. 15°.

As is also evident from the draweing the blending chamber 1 is provided at its upper end with a nozzle 7 which is arranged in the center of the end wall 3. The nozzle 7 opens out into the blending chamber 1 immediately below the inner surface of the end wall 3. Its central location provides for an outlet opening of the nozzle that is positioned along the geometric center axis of the apparatus that is common to the guide rail 6 as well as to the cylindrical shell wall 2 of the blending chamber 1. The nozzle 7 is a spray nozzle which generates drops in the order of magnitude of 10–80 μm which are spread in a substantially conical jet whose cone angle is approx. 15° and thus corresponds to the cone angle of the center opening of the guide rail 6. Outside the blending chamber the nozzle 7 is connected via a valve 8 to the feed lines 9,10 for liquid and gas respectively. The feed line 9 is connected to a liquid tank (not shown) and the feed line 10 is connected to a source of sterile air.

When the apparatus is placed into a packaging machine of known type, such as a packaging machine of the type which is described in the U.S. Pat. No. 3,911,642, the feed and discharge lines are connected to the machine's system of sterile air and sterilizing liquid, respectively.

The sterilizing liquid usually consists of 35% hydrogen peroxide and the sterile air is the ambient atmosphere which has been made to pass a sterile filter and has been heated to a temperature of approx. 300° C. When presterilization is to be initiated, the hot sterile air is introduced via the feed line 4 at a rate of approx. 150 m/s. Since the feed line 4 is arranged, as mentioned previously, tangentially in relation to the shell wall 2, a circulating movement will be imparted to the air. With the help of the guide rail 6 the circulating air is induced to rise upwards in the blending chamber 1 gradually to reach the discharge line 5 likewise joining tangentially. After the hot air has been allowed to pass for some time through the blending chamber 1 and the latter has been heated to substantially the same temperature as the air, that is to say 300° C., hydrogen peroxide and sterile air are fed at high pressure via lines 9 and 10, respectively, to the nozzle 7. Sterilizing liquid is injected via the outlet opening of the nozzle into the blending chamber 1 in countercurrent direction in relation to the air flow, that is to say downwards. The nozzle divides the liquid finely so that it is injected in the form of drops of a size of 10–80 μm. The nozzle 7 sprays the liquid in a substantially evenly distributed conical jet having an acute angle of approx. 15°. Since a circulating movement mainly along the walls of the blending chamber 1 has been imparted to the gas or hot air introduced into the blending chamber 1, the sterilizing liquid fed via the nozzle 7 will be introduced into the center of the circulating movement and more particularly along the centre axis of the helical movement of the gas. The smaller drops of sterilizing liquid issuing from the nozzle 7 will be blended very rapidly with the rotating hot air and be volatilized, while the medium-sized and larger drops will be spurted farther down into the blending chamber 1 before being heated to such a degree that they are volatilized. Owing to the countercurrent principle, the largest drops, when they approach the lower end of the blending chamber 1, will encounter hot air of the highest temperature, which ensures that a satisfactory volatilization will take place even of relatively larger drops of sterilizing agent. The helical movement of the hot air means that the drops, when they are captured by the hot air, are entrained out while being volatilized towards the periphery of the blending chamber where, if they have not achieved volatilization beforehand, they encounter the cylindrical shell wall 2 of the blending chamber 1 which has been heated by the hot air to a high temperature and consequently causes immediate volatilization of any remaining drops.

The injection of the sterilizing liquid into the blending chamber preferably takes place intermittently at such intervals that an air saturated with sterilizing agent of an appropriate dew point is obtained. In the intervals between the injections the cylindrical shell wall 2, owing to its great material thickness, can absorb and store thermal energy from the hot air passing. This thermal energy is utilized in subsequent injections of sterilizing liquid and has been found to make it possible to raise the dew point of the mixture further by approx. 10°.

The successive volatilizatiion and the vigorous blending and centrifugal effect at the injection of hot air into the blending chamber has proved in practice to achieve a very effective volatilization and as a result a very high dew point of the finished mixture can be maintained. Measurements show that under optimum conditions the dew point lies only one or two degrees below the theoretical upper limit which is defined by the heat content of the air (practically 60° C.). The helical guide rail serves not only for conducting gas from the inlet to the outlet in such a manner that it maintains volatilization in the most effective manner possible, but also for strongly reducing the noise level during operation.

The principles, preferred embodiments and modes of operation of the present invention have been described in the foregoing specification. The invention which is intended to be protected herein should not, however, be construed as limited to the particular forms described, as these are to be regarded as illustrative rather than restrictive. Variations and changes may be made by those skilled in the art without departing from the spirit of the present invention. Accordingly, the foregoing detailed description should be considered exemplary in nature and not as limiting to the scope and spirit of the invention as set forth in the appended claims.

What is claimed is:

1. An apparatus for volatilizing a liquid by blending the liquid with a heated gas comprising a casing having a chamber provided with feed and discharge lines for the gas so as to impart a circulating movement to the gas and, a helical shaped guide rail positioned inside said chamber and a nozzle to introduce the liquid as droplets into the circulating movement of the gas along a center axis of said helical shaped guide rail, wherein the helical guide rail is provided with a centrally located conical opening which widens in a direction opposite the nozzle, the centrally located conical opening provided with a cone angle substantially corresponding to a spreading angle imparted to said droplets by said nozzle.

2. The apparatus of claim 1 wherein the chamber is cylindrical, the guide rail positioned within the chamber runs along an interior surface of the chamber, and the nozzle is fitted in one end wall of the chamber.

3. The apparatus in accordance with claims 1 or 2, wherein the gas feed and the gas discharge lines are tangentially connected to the chamber at opposite ends of the chamber.

* * * * *